United States Patent [19]

Pernelle

[11] Patent Number: 5,302,512
[45] Date of Patent: Apr. 12, 1994

[54] AGGLUTINANT COMPLEX AS BLOOD TYPING REAGENT

[75] Inventor: Michel Pernelle, Igny, France

[73] Assignee: Pasteur Sanofi Diagnostics, Marnes La Coquette, France

[21] Appl. No.: 877,718

[22] Filed: May 4, 1992

[30] Foreign Application Priority Data

May 2, 1991 [FR] France ................... 91 05410

[51] Int. Cl.$^5$ ................ G01N 33/555; G01N 33/541
[52] U.S. Cl. .................... 435/7.25; 435/7.21; 436/533; 436/534; 436/828; 436/520; 436/536; 436/539; 436/540; 436/532
[58] Field of Search ............. 435/7.25, 7.21; 436/512, 520, 536, 538, 539, 540, 532, 547, 828, 533, 534; 530/387.1

[56] References Cited

U.S. PATENT DOCUMENTS 4,868,109  9/1989  Lansdorp ................ 435/28

OTHER PUBLICATIONS

Harlow and Lane, *Antibodies A Laboratory Manual*, chapter 15, Reagents, (1988 cold Spring Harbor Laboratory) pp. 615–623.

*Biology Methods Manual*, Metropolitan Police Forensic Science Laboratory, 109 Lainbeth Rd. London SE17LP England (1978) pp. 2-5 to 2-6.

Rose and Friedman, *Manual of Clinical Immunology*, 2nd Ed. American Soc. for Microbiology (1980, Washington DC) ch. 3 pp. 15–22.

Primary Examiner—Toni R. Scheiner
Attorney, Agent, or Firm—Wegner, Cantor, Mueller & Player

[57] ABSTRACT

The invention includes an agglutinant complex which is useful for the investigation of the antigens present on erythrocytes, and which results from affinity couplings between nonagglutinant IgG type antibodies specific for the antigen to be identified, a protein capable of binding to at least two sites on the Fc part of antibodies and an anti-immunoglobulin antibody or its fragments.

11 Claims, No Drawings

AGGLUTINANT COMPLEX AS BLOOD TYPING REAGENT

The present invention relates to an agglutinant complex, and the reagents containing it as well as their use for the identification of erythrocyte antigens, especially rare antigens, in a rapid agglutination test.

In the field of blood typing, a reagent, or test serum, is said to be agglutinant when it is capable of producing, in a saline solution an agglutination of cells carrying the antigen which is specific for the antibody present in the test serum; this is the most frequently observed behaviour for reagents containing IgM type antibodies; in contrast, IgG type antibodies are generally not agglutinant even after a certain period of incubation.

In this case, and in particular for membrane antigens which are either in small numbers on each cell, or are not very accessible to antibodies, the agglutination has to be induced using means such as the addition of proteolytic enzymes or high protein concentrations into the medium, or alternatively by using chemically modified IgG molecules, as in WO 90/07118 and EP-A 022,669.

There are many examples of antigens which are difficult to detect on blood cells. For red blood cells, the antigens of the Rhesus (Rh), Lutheran, Kell (K), Duffy, Kidd and Diego systems and the like may be mentioned.

It is desirable to identify these antigens, sometimes even in an emergency, prior to a blood transfusion, at least in the recipients of multiple blood transfusions, and prior to any organ transplantation, or when there is a risk of foetomaternal-alloimmunisation. Accordingly, a rapid technique which is simple to use and inexpensive, such as those enabling the existence of an immunological reaction to be established directly by virtue of the generation of an agglutination, which uses an agglutinant reagent that is specific, stable and of low production cost, is of great interest.

It is known that an erythrocyte typing may be carried out using various simple and rapid methods which may even be automated when the reagent is agglutinant. For a description of these methods, reference may be made to the manual by Rouger P. and Salmon C.: Techniques de Laboratoire 6 p. 25-26 Ed. Masson (1981), which describes in particular the reactions on opaline plates, in tubes or in microplates.

However, the reagents which can be used in these techniques must be based on IgM type antibodies, those of the IgG type not being agglutinant. Accordingly, it can be observed that the reagents currently marketed apply solely to ABO or Rhesus typings, for which systems the IgM type polyclonal antibodies are naturally abundant in the human organism and, especially, for which monoclonal antibodies may be obtained through the culture of hybridomas.

On the other hand, the production of IgM type polyclonal antibodies in sufficient quantity to meet marketing requirements for a blood-typing reagent in the case of antigens which are difficult to detect would require the voluntary immunisation of a large number of people to enable IgM antibodies which are specific for the antigen to be recovered from their blood samples: these specific IgM antibodies would, in addition, then have to be separated from all the other IgM antibodies present before they could be used. Furthermore, these expensive operations would have to be repeated indefinitely in a reproducible manner since the preparation of IgM type monoclonal antibodies is not presently known for most of these antigens.

An erythrocyte typing taking into consideration antigens for which only IgG type antibodies, and therefore nonagglutinant reagents, are available in a sufficient amount, can only be carried out using more complex techniques which are described in the above manual p. 33-34 and 49 to 65; among them, there may be mentioned reactions on opaline plates, at 40° C., in the presence of high concentrations of proteins or other polymers including albumin, reactions in the presence of proteolytic enzymes including papain or so-called antiglobulin reaction (Coombs test) and analogues thereof.

Means have also been proposed for producing an agglutinant reagent from IgG type antibodies.

For example, it has been disclosed in Proc. Natl. Acad. Scien. USA 74 (6) p. 2531-2535 (1977) that the reduction of IgG by 2-mercaptoethanol rendered it agglutinant; but this method, which is(on the whole) complex because it involves a chemical reaction, does not give the expected result for antigens which are not very flexible or which are present on a small number of sites per cell, such as the K antigen; in addition, the method which is carried out in tubes entails a microscope reading after incubating for 2 hours.

An agglutinant reagent consisting of IgG antibodies fixed by their Fc region to protein A is described in GB-A-2,103,360; but in this case also, the agglutination is not immediate; it may be observed, in tubes, only after incubating for 45 minutes at 37° C.; in addition, the nonhomogeneous nature of the reagent, which is prepared with whole bacteria, does not permit easy use, especially in automated equipment. On the other hand, when protein A is isolated from its bacterial cell, rare antigens such as K antigen do not produce agglutination.

The present invention, according to a first feature, relates to an agglutinant complex and the agglutinant reagents containing it, for the identification of erythrocyte antigens by simple and rapid agglutination techniques which can only be carried out using IgM type antibodies.

The complex according to the invention may obviously also be used in more complex but more sensitive conventional techniques whose use is sometimes required to confirm a doubtful result.

The agglutinant complex according to the invention results from affinity couplings between an IgG type antibody which is specific for the antigen to be identified or assayed, a protein capable of binding to at least two locations on the Fc part of antibodies and an anti-immunoglobulin antibody.

The IgG type antibodies may be monoclonal or polyclonal.

When monoclonal antibodies are used, they are obtained in a conventional manner from ascites liquids or supernatants which are preferably clarified, of suitable hybridoma cell cultures; IgG monoclonal antibodies which are specific for blood types that are difficult to identify are available commercially; others are described in the literature. The IgG oolyclonal antibodies may be extracted from sera or plasmas of human subjects immunised, for example, by the absorption-elution method described in Vox. Sang. 33 p. 280 (1977); they are rarer and more expensive.

The complex and the reagents according to the invention containing it are particularly useful for the identification of erythrocyte antigens which are difficult to detect and especially those of the Kell, Duffy or Kidd systems for which spontaneously immunised and IgM-carrying humans are rare and for which no IgM type monoclonal antibodies are known which are of sufficient quality to permit recognition of blood cells.

Among the proteins capable of becoming fixed to the Fc part of antibodies and which carry at least two fixation sites for forming a macromolecular lattice structure during the immunological reaction with the antigen to be detected, there may be mentioned those of microbiological origin and especially protein A from *Staphylococcus aureus*, which is well known, or those from *Staphylococcus epidermidis* and from *Scaphylococcus pyogenes* or alternatively protein G from Streptococcus species; these proteins have many binding sites.

Natural proteins or fragments thereof will be preferably isolated from bacterial cells and purified especially so as to have reproducible batches, but they may also be recombinant proteins; various proteins are marketed, especially by the Companies SIGMA or PIERCE, generally in freeze-dried form.

The antiglobulin antibody, which is another constituent of the complex, may be chosen from all anti-immunoglobulin, polyvalent antibody types or from those which are specific for IgG antibodies; it may be of monoclonal or polyclonal origin and be more or less purified; fragments, containing the F(ab) part or such as F(ab')2 may also be used. When the IgG antibody directed against the antigen to be identified is of human origin, the antiglobulin antibody will be directed against the immunoglobulins of human origin; it is indeed important to have the same species specificity for the two antibodies of the complex unless interspecies affinity reactions were possible.

The agglutinant complex according to the invention may be prepared by adding the protein, which is capable of binding to the Fc part of antibodies, to a solution of the IgG antibody directed against the antigen to be detected, in aqueous medium, preferably buffered to a pH of between 5 and 9, preferably between 6.5 and 7.5, or in substantially isotonic, optionally buffered, aqueous saline medium; the reaction is completed after a period which depends especially on the concentrations and the incubation temperature which is generally between 4° C. and 50° C., preferably between 20° C. and 40° C.; in the latter temperature range, the time required for the formation of bonds is between 5 min and 1 hour.

The amount of protein added to the solution of antibody depends on the antibody concentration but also on the density of antibody-binding sites on the protein; it is preferable that the antibodies substantially saturate all the sites. By way of example, it may be mentioned that the ratio of the weight of antibody to the weight of pure protein A or G will generally be between .3 and 30, preferably between 5 and 20, and that the concentration of antibody in the binding medium will be preferably greater than 50 µg/ml.

The addition of the anti-IgG may take place immediately after the end of the first incubation, or later on, if the medium is preserved at +4° C. or preferably frozen. As in the first stage, the volume and the concentration of the solution of antibody to be added depends especially on the specificity of the antibody and on the sensitivity desired. For example, for a Kell or Rhesus typing, substantially identical amounts of IgG type antibody and anti-immunoglobulin may be used for forming the complex according to the invention.

The temperature and the duration of the second incubation to bind the anti-antibody are not critical; they may vary within the same limits as those indicated for the protein/first antibody binding. A person skilled in the art will be able to determine all the parameters for the preparation of the complex by preliminary tests.

It may also be possible, although this method is not preferred, to incubate a mixture of the two antibodies and the protein, in suitable proportions, so as to obtain the agglutinant complex.

The solution of agglutinant complex obtained at the end of the affinity couplings is generally more concentrated than that which will be used in rapid routine identification methods for which the concentration of complexed IgG in the reagent is advantageously about 1 to 50 µg/ml.

Accordingly, once it has been prepared, it may be preserved at a temperature of less than 10° C. and even frozen for subsequent dilution immediately before use, or it may be preserved in dilute form, ready for use, under the same conditions after packaging into multiple unit doses. The appropriate dilution is generally obtained by adding, to the medium for preparing the complex, a TRIS- or phosphate-based buffer solution having a pH of between 5 and 9, which may also contain water-soluble salts, amino acids as well as macromolecules which are known for their ability to stabilise antibody solutions and to enhance agglutination reactions at lower concentration than usual, that is to say, in general, at a concentration of less than 5%; at these low concentrations, no false positives are formed in the presence of IgG in the serum to be tested. Among these macromolecules, there may be mentioned polyvinylpyrrolidone, neutral polysaccharides such as dextran or proteins such as albumin, which are well known to the specialist.

A bacteriostatic agent such as sodium azide is also preferably added for prolonged preservation.

These reagents and the agglutinant complex of the invention may also be preserved in freeze-dried form; in that case, they are introduced at the time of use in distilled water or in a phosphate type buffered saline which is common in this technical domain.

According to another of its features, the invention relates to a method for the identification and the assay of antigens on red blood cells, which consists in placing the erythrocytes and the agglutinant complex according to the invention in contact with a suitable medium and in observing if an agglutination is produced.

The composition of the medium in which the agglutination may occur is not critical; however, the cells must remain intact therein, which generally requires the presence of inorganic salts; moreover, it has been observed that the presence of macromolecules, in a small amount, less than 5%, increased the reaction rate; the nature of these macromolecules and their concentration depends on the nature of the antibody, on the complex, on its concentration and on the operating conditions, but a person skilled in the art will be able to choose them following preliminary tests.

This method is advantageously carried out for erythrocyte typing and especially for investigating the presence of antigens of the Rh, Duffy, Kidd, or Kell systems for which this simple and rapid method gives results which are equivalent to most methods currently used in laboratories, hospitals and blood transfusion centres.

Any one of the known rapid techniques for IgM-based blood typing may be used to carry out the immunological reaction and to visualise the agglutination, whether on opaline plates, in tubes or in microplates. The procedure may be carried out at a temperature of between 10° C. and 37° C., but room temperature, which is simpler to use, is preferred; the agglutination is, in this case, observed rapidly, within one minute to a few minutes depending on the operating conditions, the affinity of the antibody, the nature of the antigen and its concentration in the sample.

In the following text, examples of agglutinant complexes and of reagents of the invention and the results of carrying out the method according to the invention for the identification of rare antigens, compared with those obtained with agglutinant polyclonal reagents rich in IgM type antibodies, are described.

The different agglutination reactions used in the examples were carried out as follows:

1) Reaction on opaline plates at room temperature:

A drop of reagent and a drop of the washed or unwashed, globular pellet to be tested, are deposited on the plate and mixed with a glass rod to form a circle 2 cm in diameter; the agglutination which may occur is detected after 2 minutes.

2) Reaction in tubes:

A drop of 2% erythrocyte suspension and a drop of reagent are mixed and the agglutinates which may form after 1 or 2 hours of sedimentation are observed.

3) Antiglobulin reaction (or Coombs test):

A drop of suspension, in physiological solution, of washed or unwashed red blood cells to be tested, is added to a Kahn tube containing a drop of reagent and the mixture is incubated for 15 minutes at 37° C. before washing it three times with physiological solution. 1 drop of antiglobulin is added to the decantation pellet and the mixture is centrifuged for 1 minute after resuspending the pellet; the agglutination which may occur is then observed by shaking the tube gently.

The titres and scores of the reactions were calculated in a conventional manner as described especially in the abovementioned manual by Rouger P. and Salmon C., p. 31-32.

EXAMPLE 1

Anti-Kell Agglutinant Reagent a) Preparation

The clarified supernatant of a cell culture containing 150 µg/ml of an IgG type anti-Kell monoclonal antibody of human origin, directed against the K antigen, is diluted by adding phosphate buffered saline (pH 7.4) up to an antibody concentration of 100 µg/ml. One volume of a solution containing, in the same buffer, 10 µg/ml of protein A, which is marketed by Sigma under the reference P 6031, is added to this solution; the mixture is maintained stirring for 60 minutes at 37° C., and then 1 volume of a solution of polyvalent antiglobulin is added and the mixture is maintained stirring for 30 minutes at 37° C. before re-equilibrating it to room temperature, at around 20° C.

The polyvalent antiglobulin is a reagent prepared from goat serum which is diluted in isotonic saline solvent containing albumin, the said goat having been hyper-immunised with human immunoglobulins and complement. The characteristics of this reagent correspond to the definitions of the Official Journal of the French Republic of 17 Mar. 1984, under the heading of Ministry of Social Affairs—characteristics and standards of reagents used in erythrocyte immunohaematology (appendix 2—p. 2596); this reagent is marketed by Diagnostics Transfusion (FR) under the reference 21120.

For the tests whose results are presented in the following text, the mixture thus obtained was diluted before use with the same volume of phosphate buffered saline (pH 7.4) containing glycocoll (2%) and dextran (1%). The reference reagent, prepared from hyperimmune human sera and enriched with macromolecules, is marketed by Diagnostics Transfusion under the reference 21083.

b) Agglutination Tests

1) Reaction on opaline plates at room temperature:

of 200 blood samples from donors, of which 8% are known to be of the K+ phenotype, 100% positive phenotypes were identified using the reagent according to the invention and the reference reagent, with no false positives or negatives. During this study, it was observed that 45% of the agglutination images obtained with the reagent according to the invention were more distinct and 50% were equivalent.

the time taken for the formation of the first agglutinates with the two reagents was short: 5 seconds for the product of this example, 6 seconds for the reference.

the titres were 8 and 4 and the scores 20 and 14 for the product of this example and for the reference, respectively.

If, instead of the complex according to the invention, the reagent contains the IgG used for its preparation or this IgG bound to protein A alone, no agglutination is observed under these conditions.

2) Reaction in tubes and reading using an optical microscope:

The results obtained are:

| | Titre | Score |
|---|---|---|
| Reagent of Example 1 | 256 | 66 |
| Reference reagent | 128 | 56 |

3) Antiglobulin reaction:

| | Titre | Score |
|---|---|---|
| Reagent of Example 1 | 128 | 57 |
| Reference reagent | 256 | 71 |

EXAMPLE 2

Anti-Kell Agglutinant Reagent

A reagent is prepared according to the process described in Example 1, but replacing protein A by pure, commercially available protein G.

In the reaction on opaline plates, the reagent has a titre of 8 and a score of 20 while in tubes, its titre is 128 and its score 52; in the antiglobulin reaction, the titre is 128 and the score 56.

EXAMPLE 3

Anti-Kell Agglutinant Reagent

A reagent is prepared according to the method described in Example 1 using protein A and an anti-IgG anti-immunoglobulin H+L, directed against the heavy and light chains, of human origin, marketed by Biosys France under the reference BI 2015.

On opaline plates, the titre is 8 and the score 20; in tubes, the titre is 128 and the score 49; in the antiglobulin reaction, the titre is 64 and the score 46.

EXAMPLE 4

Reagent for Investigating the Phenotype D (Rh+)

The reagent was prepared using an IgG type monoclonal antibody directed against antigen D, a polyvalent human anti-immunoglobulin and protein A, by applying the method described in Example 1.

A reagent prepared under the same conditions using only the starting monoclonal antibody in the reaction on opaline plates, does not produce agglutination, whereas the reagent of the present example has a titre of 16 and a score of 30; in the more complex antiglobulin reaction, the starting monoclonal antibody has a slightly higher score than that of the reagent of the present example.

I claim:

1. Agglutinant complex for the identification of antigens on erythrocytes, comprising an IgG antibody that is specific for the antigen to be identified, a protein selected from the group consisting of proteins A and G and an anti-immunoglobulin antibody or its antigen-binding fragments, bound directly through affinity bonds.

2. Complex according to claim 1, in which the two antibodies have the same species specificity.

3. Complex according to claim 1, in which the anti-immunoglobulin antibody is specific for IgG.

4. Complex according to claim 1, in which the IgG antibody is speciforan antigen of the Kell, Duffy or Kidd systems.

5. Complex according to claim 4, in which the antigen is of the Kell System.

6. Agglutinant reagent comprising a complex according to claim 1, at a concentration corresponding to 1 to 50 µg/ml of IgG in a saline solution buffered to a pH of between 5 and 9 and containing 0 to 5% of agglutination enhancing macromolecules.

7. Reagent according to claim 6, which contains macromolecules selected from the group consisting of polyvinylpyrrolidone, neutral polysaccharides and proteins.

8. Process for producing a complex according to claim 1 comprising the steps of mixing the IgG antibody specific for the antigen to be identified with the protein under conditions for forming affinity couplings followed by mixing the resulting coupled product with the anti-immunoglobulin antibody under conditions for forming affinity couplings.

9. Method for the identification of antigens on the wall of erythrocytes comprising mixing an agglutinant complex according to claim 1 with the erythrocytes to be characterized and observing the agglutination which may occur.

10. Method for the identification of a Kell antigen in a blood sample comprising mixing the sample with an agglutinant reagent according to claim 6 and observing the agglutination which may occur.

11. Method according to claim 10, which is carried out on plates.

* * * * *